United States Patent
Yonce

(10) Patent No.: US 9,180,294 B2
(45) Date of Patent: Nov. 10, 2015

(54) ELECTRICAL STIMULATION DEVICE HAVING MULTIPLE STIMULATION CHANNELS

(71) Applicant: AMS Research Corporation, Minnetonka, MN (US)

(72) Inventor: David J. Yonce, Edina, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 14/352,594

(22) PCT Filed: Oct. 16, 2012

(86) PCT No.: PCT/US2012/060363
§ 371 (c)(1),
(2) Date: Apr. 17, 2014

(87) PCT Pub. No.: WO2013/059158
PCT Pub. Date: Apr. 25, 2013

(65) Prior Publication Data
US 2014/0257424 A1    Sep. 11, 2014

Related U.S. Application Data

(60) Provisional application No. 61/549,310, filed on Oct. 20, 2011.

(51) Int. Cl.
*A61N 1/00* (2006.01)
*A61N 1/36* (2006.01)

(52) U.S. Cl.
CPC ......... *A61N 1/36007* (2013.01); *A61N 1/36125* (2013.01)

(58) Field of Classification Search
CPC .................................. A61N 1/36007
USPC ...................................................... 607/40, 41
See application file for complete search history.

(56) References Cited

U.S. PATENT DOCUMENTS 6,354,991 B1    3/2002    Gross et al.
6,652,449 B1    11/2003    Gross et al.
(Continued)

FOREIGN PATENT DOCUMENTS

WO    2010019867 A1    2/2010
WO    2013059158 A1    4/2013

OTHER PUBLICATIONS

International Search Report and Written Opinion of PCT/US2012/060363 mailed Jan. 18, 2013.

*Primary Examiner* — Nicole F. Lavert
*Assistant Examiner* — Nadia A Mahmood
(74) *Attorney, Agent, or Firm* — Westman, Champlin & Koehler, P.A.

(57) ABSTRACT

An implantable electrical stimulation device configured to treat multiple pelvic conditions of a patient includes a pulse generator, memory, first and second electrode leads comprising one or more electrodes, a switch and a controller. The switch has a first state, in which the first electrode lead is electrically coupled to the pulse generator, and a second state, in which the second electrode lead is electrically coupled to the pulse generator. The controller includes at least one processor that is configured to execute at least one stimulation program stored in the memory. The controller is also configured to selectively set the switch in the first or second state. Electrical stimulation pulses generated by the pulse generator responsive to the execution of the stimulation program are delivered to the first or second electrode lead depending on the state of the switch.

11 Claims, 3 Drawing Sheets

(56) References Cited

U.S. PATENT DOCUMENTS

| | | |
|---|---|---|
| 6,896,651 B2 | 5/2005 | Gross et al. |
| 2006/0161219 A1 | 7/2006 | Mock et al. |
| 2006/0229687 A1 | 10/2006 | Goetz et al. |
| 2008/0103574 A1 | 5/2008 | Gerber |
| 2010/0106231 A1 * | 4/2010 | Torgerson et al. ............ 607/116 |
| 2011/0071589 A1 * | 3/2011 | Starkebaum et al. ........... 607/40 |

* cited by examiner

ELECTRICAL STIMULATION DEVICE HAVING MULTIPLE STIMULATION CHANNELS

CROSS-REFERENCE TO RELATED APPLICATION

This Application is a Section 371 National Stage Application of International Application No. PCT/US2012/060363, filed Oct. 16, 2012 and published as WO 2013/059158 A1 on Apr. 25, 2013, in English, which claims the benefit of U.S. Provisional Application Ser. No. 61/549,310, filed Oct. 20, 2011 under 35 U.S.C. §119(e). The contents of which are hereby incorporated by reference in their entirety.

BACKGROUND

Electrical stimulation devices have been used to deliver electrical stimulation therapies for the purpose of treating a variety of pelvic conditions such as urinary and fecal incontinence. A typical electrical stimulation system includes one or more implantable medical leads coupled to an external or implantable electrical stimulator device. The implantable lead may be percutaneously or surgically implanted in a patient on a temporary or permanent basis such that an electrode is positioned at a single target stimulation site. Electrical pulses can be generated by the device and delivered to the target stimulation site through the electrode to perform the electrical stimulation therapy and treat the condition of the patient. For instance, urinary incontinence can be treated through electrical stimulation of the urinary sphincter. Likewise, fecal incontinence can be treated through electrical stimulation of the anal sphincter.

Some patients have both urinary incontinence and fecal incontinence, or initially have one of the conditions and then later develop the other. Conventional electrical stimulation devices are only configured to apply electrical stimulation therapies to a single targeted site (e.g., urinary sphincter or anal sphincter) to treat the associated condition. Thus, patients requiring treatment for both urinary incontinence and fecal incontinence require a stimulation device for each of the conditions in order to deliver two separate electrical stimulation therapies to treat the conditions.

SUMMARY

Embodiments of the invention are directed to an implantable electrical stimulation device that is configured to treat multiple pelvic conditions of a patient and methods of using the device to treat multiple pelvic conditions of a patient. One embodiment of the device includes a pulse generator (106), memory (104), first and second electrode leads (110, 112) comprising one or more electrodes (114), a switch (124) and a controller (102). The switch has a first state, in which the first electrode lead is electrically coupled to the pulse generator, and a second state, in which the second electrode lead is electrically coupled to the pulse generator. The controller includes at least one processor that is configured to execute at least one stimulation program (120, 122) stored in the memory. The controller is also configured to selectively set the switch in the first or second state. Electrical stimulation pulses generated by the pulse generator responsive to the execution of the stimulation program are delivered to the first or second electrode lead depending on the state of the switch.

Another embodiment of the implantable electrical stimulation device comprises first and second pulse generators (106A, 106B), memory (104) and a controller (102). The controller includes at least one processor that is configured to execute at least one stimulation program (120, 122) stored in the memory. The first and second pulse generators are each configured to produce stimulation pulses responsive to the execution of the at least one stimulation program.

In one embodiment of the method, an electrical stimulation device (100) comprising a control unit (101) and first and second electrode leads (110, 112) is implanted (130) in a patient. In one embodiment, the first electrode lead comprises one or more electrodes (114) positioned at a first stimulation site (116), and the second electrode lead comprises one or more electrodes (114) positioned at a second stimulation site (118) that is different from the first stimulation site. A first stimulation treatment is performed (132) that comprises delivering electrical stimulation signals to the first stimulation site through the first electrode lead. A first pelvic condition of a patient is treated (134) responsive to the first stimulation treatment. A second stimulation treatment is also performed (136) comprising delivering electrical stimulation signals to the second stimulation site through the second electrode lead. A second pelvic condition of the patient is treated (138) responsive to the second stimulation treatment.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
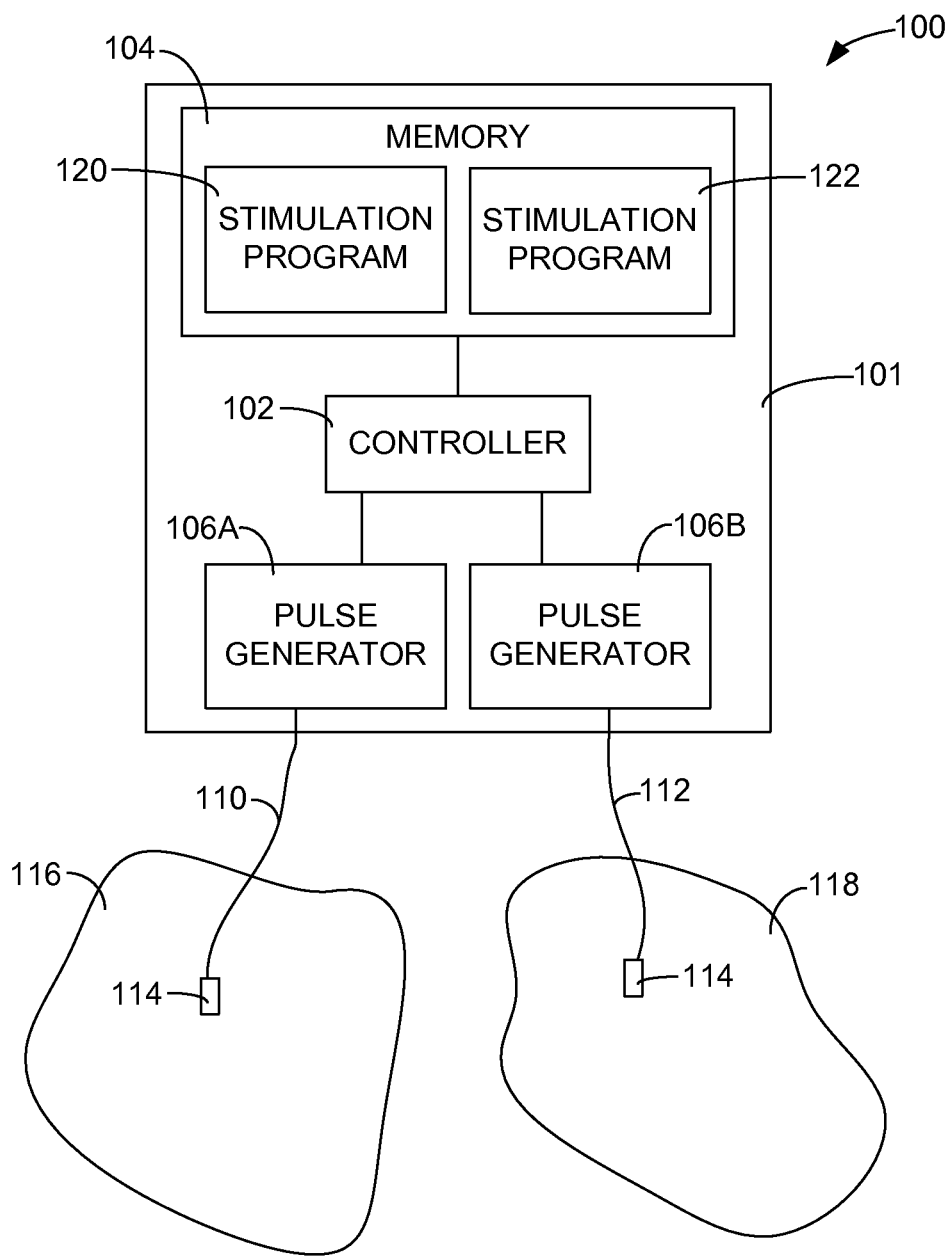
FIGS. 1 and 2 are simplified block diagrams of electrical stimulation devices formed in accordance with embodiments of the invention.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Figure 2:
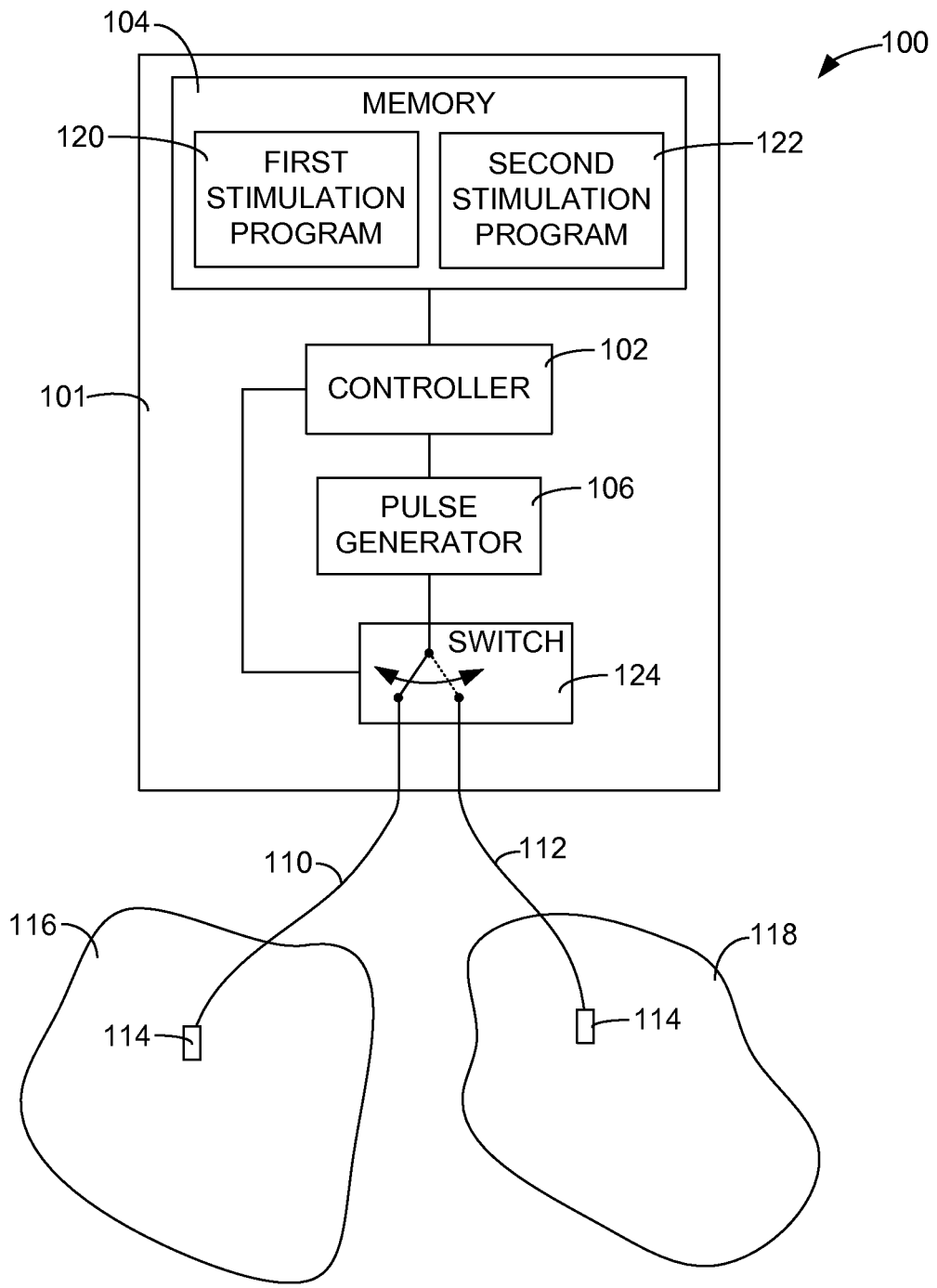

FIGS. 1 and 2 are block diagrams of electrical stimulation devices 100 formed in accordance with embodiments of the invention. Some conventional components are not shown in order to simplify the illustrations, such as a battery used to power the circuitry of the device 100, communications circuitry configured to receive and/or transmit data to a programmer located externally to the patient, and other conventional implantable stimulator components.

In one embodiment, the device 100 includes a control unit 101 that includes a hermetically sealed housing that protects the circuitry of the control unit 101 when the device 100 is implanted within a patient. In one embodiment, the circuitry includes a controller 102, memory 104, and one or more pulse generators 106.

The controller 102 includes one or more processors that are configured to execute program instructions that are stored in the memory 104 and/or communicated to the device 100 from an external programmer. Various functions and method steps described herein are performed by the device 100 responsive to the execution of the program instructions by the one or more processors of the controller 102. The programs stored in the memory 104 may be configured prior to implantation of the device 100 in the patient, or configured or revised after implantation of the device 100 using a suitable programmer in accordance with conventional techniques.

In one embodiment, at least two electrode leads 110 and 112 are coupled to the control unit 101. The electrode leads 110 and 112 each include one or more electrodes 114. Electrical pulses generated by the one or more pulse generators 106 can be delivered to a target stimulation site of the patient, such as separate target sites 116 and 118, through the electrodes 114. The electrode leads 110 and 112 may include a conventional tissue anchor, such as a helical coil or other fixation component, that resists migration of the distal ends of the electrode leads within the tissue of the patient.

In one embodiment, the target sites 116 and 118 are selected based upon the pelvic condition to be treated. In one embodiment, when the electrical stimulation therapy is configured to treat urinary incontinence of a patient, the target site may be the urinary sphincter of the patient, or one or more nerves that innervate the urinary sphincter of the patient. When the pelvic condition to be treated in response to the electrical stimulation therapy is fecal incontinence, the target site may be the anal sphincter of the patient, or one or more nerves that innervate the anal sphincter of the patient. When the pelvic condition to be treated by the electrical stimulation therapy is urinary retention, the target site may be bladder muscles of a patient, which are relaxed in response to the electrical stimulation therapy. When the pelvic condition of the patient to be treated by the electrical stimulation therapy is pain due to interstitial cystitis, the target site may be one or more muscles of the pelvic floor, such as the levator ani. Other target sites within the pelvic region may be selected as the target site 116 or 118 in accordance with conventional pelvic condition stimulation treatments.

In one embodiment, the memory 104 includes at least two stimulation programs, such as a first stimulation program 120 and a second stimulation program 122. Electrical stimulation pulses are generated by the at least one pulse generator 106 in response to the execution of each of the stimulation programs 120 and 122 by the one or more processors of the controller 102. In one embodiment, the electrical stimulation pulses generated in response to the execution of the first stimulation program 120 are delivered to the target site 116 through the electrode lead 110, and the electrical pulses generated in response to the execution of the second stimulation program 122 are delivered to the target site 118 through the electrode lead 112.

In one embodiment, the stimulation pulses generated in response to the execution of the first stimulation program 120 are configured to treat a first pelvic condition of the patient, and the stimulation pulses generated in response to the execution of the second stimulation program 122 are configured to treat a second pelvic condition that is different from the first pelvic condition. Exemplary embodiments of the first and second pelvic conditions include urinary incontinence, fecal incontinence, pain due to interstitial cystitis, urine retention, and other pelvic conditions that are treatable through an electrical stimulation therapy. The electrical stimulation pulses generated by the one or more pulse generators 106 may be in accordance with conventional stimulation therapies, such as those described in U.S. Pat. Nos. 6,652,449, 6,354,991 and 6,896,651, for example.

In one embodiment, the stimulation device 100 includes at least two pulse generators 106, such as pulse generator 106A and pulse generator 106B, as shown in FIG. 1. In one embodiment, the pulse generators 106A and 106B are substantially distinct electrical pulse generator circuits that are each configured to generate electrical stimulation pulses for treating a pelvic condition of a patient responsive to the execution of a stimulation program stored in memory 104. Each of the pulse generators 106A and 106B may be formed in accordance with conventional pulse generators.

In one embodiment, the pulse generator 106A generates electrical stimulation pulses in response to the execution of the stimulation program 120 by the controller 102. In one embodiment, the device 100 is configured to electrically couple the electrode lead 110 to the pulse generator 106A, or the electrode lead 110 is electrically coupled to the pulse generator 106A. Accordingly, the electrode lead 110 receives the stimulation pulses generated by the pulse generator 106A. As a result, the electrical stimulation pulses generated by the pulse generator 106A in response to the execution of the stimulation program 120 are delivered to the target site 116 through the electrode lead 110 and the corresponding electrodes 114.

In one embodiment, the pulse generator 106B generates electrical stimulation pulses in response to the execution of the stimulation program 122 by the controller 102. In one embodiment, the device 100 is configured to electrically couple the electrode lead 112 to the pulse generator 106B, or the electrode lead 112 is electrically coupled to the pulse generator 106B. Accordingly, the electrode lead 112 receives the stimulation pulses generated by the pulse generator 106B. As a result, the electrical stimulation pulses generated by the pulse generator 106B in response to the execution of the stimulation program 122 are delivered to the target site 118 through the electrode lead 112 and the corresponding electrodes 114.

In accordance with another embodiment, the device 100 includes a single pulse generator 106 and a switch 124, as illustrated in FIG. 2. In accordance with this embodiment, electrical stimulation pulses are generated by the pulse generator 106 and delivered to the switch 124, which directs the stimulation pulses to either the electrode lead 110 implanted at the stimulation site 116, or the electrode lead 112 implanted at the stimulation site 118.

The switch 124 can be any suitable electrical component or circuit configured to perform the desired switching function, and may comprise semiconductor transistors and other conventional components. In one embodiment, the switch 124 has a first state, in which the electrode lead 110 is electrically coupled to the pulse generator 106 and, thus, is configured to receive the stimulation pulses generated by the pulse generator 106. While the switch is in the first state, the electrode lead 112 is electrically disconnected from the pulse generator 106. That is, stimulation pulses generated by the pulse generator 106 are not delivered directly to the electrode lead 112 through the switch 124.

In one embodiment, the switch 124 has a second state, in which the electrode lead 112 is electrically coupled to the pulse generator 106 and, thus, is configured to receive electrical stimulation pulses generated by the pulse generator 106. While the switch is in the second state, the electrode lead 110 is electrically disconnected from the pulse generator 106. That is, stimulation pulses generated by the pulse generator 106 are not delivered directly to the electrode lead 110 through the switch 124.

In one embodiment, the controller 102 is configured to set the switch 124 in either the first or second state depending upon the stimulation program being executed. In one embodiment, the controller 102 sets the switch in the first state in response to, or in preparation of, the execution of the stimulation program 120, and sets the switch 124 in the second state in response to, or in preparation of, the execution of the stimulation program 122. As a result, electrical stimulation pulses that are generated by the pulse generator 106 in response to the execution of the stimulation program 120 are delivered to the target site 116 through the switch 124, the electrode lead 110 and its corresponding electrodes 114. Likewise, electrical stimulation pulses generated by the pulse generator 106 in response to the execution of the stimulation program 122 are delivered to the target site 118 through the switch 124, the electrode lead 112 and the corresponding electrodes 114.

Figure 3:
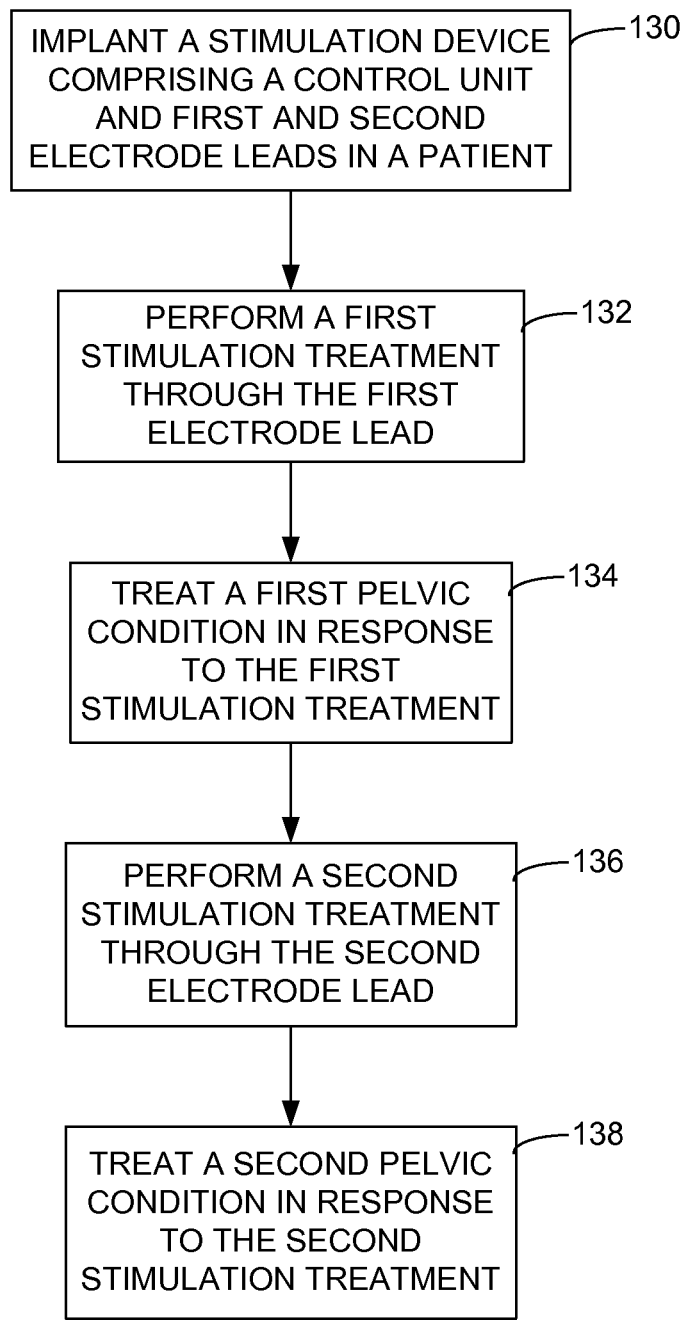
FIG. 3 is a flowchart illustrating a method of treating multiple pelvic conditions of a patient in accordance with embodiments of the invention.

Another embodiment of the invention is directed to a method of treating multiple pelvic conditions of a patient using the stimulator device 100 formed in accordance with the embodiments described above with regard to FIGS. 1 and 2. FIG. 3 is a flowchart illustrating the method in accordance with embodiments of the invention.

At 130 of the method, the stimulation device 100 comprising a control unit 101 and first and second electrode leads 110 and 112 are implanted in a patient. In one embodiment, the device 100 is implanted in the pelvic region of a patient. In one embodiment, the electrodes 114 of the electrode lead 110 are implanted in a target site 116 of the patient, and the electrodes 114 of the electrode lead 112 are implanted in a target site 118 of the patient that is different from the target site 116, as described above.

At 132 of the method, a first stimulation treatment is performed through the first electrode lead 110. When the device 100 is formed in accordance with the embodiment described above with regard to FIG. 1, step 132 involves generating electrical stimulation pulses using the pulse generator 106A in response to the execution of the stimulation program 120 by the one or more processors of the controller 102. The stimulation pulses generated by the pulse generator 106A are delivered to the target site 116 through the electrode lead 110.

In accordance with another embodiment, step 132 is performed using the device 100 described above with reference to FIG. 2. In accordance with this embodiment, electrical pulses are generated by the pulse generator 106 in response to the execution of the stimulation program 120 by the one or more processors of the controller 102. The controller 102 also sets the switch 124 in the first state to electrically couple the pulse generator 106 to the electrode lead 110. The stimulation pulses generated by the pulse generator 106 are delivered to the target site 116 through the switch 124 and the electrode lead 110 to perform the first stimulation treatment.

At 134, a first pelvic condition is treated in response to the first stimulation treatment. The first pelvic condition treated in step 134 may be any of those described above.

At 136 of the method, a second stimulation treatment is performed through the second electrode lead 112. When the device 100 is formed in accordance with the embodiments described above with reference to FIG. 1, step 136 involves generating electrical stimulation pulses using the pulse generator 106B in response to the execution of the stimulation program 122 by the one or more processors of the controller 102. The stimulation pulses generated by the pulse generator 106B are delivered to the elect target site 118 through the electrode lead 112 and the corresponding electrodes 114.

When the device 100 is formed in accordance with the embodiments described above with regard to FIG. 2, step 136 involves generating electrical stimulation pulses using the pulse generator 106 in response to the execution of the stimulation program 122 by the one or more processors of the controller 102. In one embodiment, the controller 102 sets the switch 124 in the second state such that the stimulation pulses generated by the pulse generator 106 are delivered to the target site 118 through the switch 124 and the electrode lead 112.

At 138 of the method, a second pelvic condition of a patient is treated in response to the second stimulation treatment. The second pelvic condition may be selected from any of those described above.

Although the present invention has been described with reference to preferred embodiments, workers skilled in the art will recognize that changes may be made in form and detail without departing from the spirit and scope of the invention. For example, the device 100 may include more than two pulse generators, each configured to deliver stimulation pulses to a separate electrode lead.

What is claimed is:

1. Implantable electrical stimulation device comprising:
   a pulse generator;
   memory containing a first stimulation program and a second stimulation program;
   first and second electrode leads each comprising one or more electrodes;
   a switch having a first state in which the first electrode lead is electrically coupled to the pulse generator, and a second state in which the second electrode lead is electrically coupled to the pulse generator; and
   a controller comprising at least one processor configured to execute the first and second stimulation programs stored in the memory, the controller configured to selectively set the switch in the first or second state;
   wherein:
      electrical stimulation pulses generated by the pulse generator are delivered to the first electrode lead responsive to the execution of the first stimulation program by at least one processor when the switch is in the first state;
      electrical stimulation pulses generated by the pulse generator and delivered to the second electrode lead responsive to the execution of the second stimulation program by the at least one processor when the switch is in the second state;
      the stimulation pulses generated by the pulse generator in response to the execution of the first stimulation program are configured to treat a first pelvic condition; and
      the stimulation pulses produced by the pulse generator in response to the execution of the second stimulation program are configured to treat a second pelvic condition that is different from the first pelvic condition.

2. The device of claim 1, wherein the first and second pelvic conditions are selected from the group consisting of urinary incontinence, fecal incontinence, pain due to interstitial cystitis and urine retention.

3. An implantable electrical stimulation device comprising:
   first and second pulse generators;
   memory containing a first stimulation program and a second stimulation program; and
   a controller comprising at least one processor configured to execute the first and second stimulation programs stored in the memory;
   wherein:
      the first pulse generator produces stimulation pulses responsive to the execution of the first stimulation program by the at least one processor;
      the second pulse generator produces stimulation pulses responsive to the execution of the second stimulation program by the at least processor;
      the stimulation pulses produced by the first pulse generator in response to the execution of the first stimulation program are configured to treat a first pelvic condition; and
      the stimulation pulses produced by the second pulse generator in response to the execution of the second stimulation program are configured to treat a second pelvic condition that is different the first pelvic condition.

4. The device of claim 3, wherein the first and second pelvic conditions are selected from the group consisting of urinary incontinence, fecal incontinence, pain due to interstitial cystitis and urine retention.

5. The device of claims 3, further comprising:
   at least a first electrode lead comprising one or more electrodes electrically coupled to the first pulse generator; and
   at least a second electrode lead comprising one or more electrodes electrically coupled to the second pulse generator.

6. A method of treating pelvic conditions of a patient comprising:
   implanting an electrical stimulation device comprising a control unit and first and second electrode leads in a patient, wherein the first electrode lead comprises one or more electrodes positioned at a first stimulation site, and the second electrode lead comprises one or more electrodes positioned at a second stimulation site that is different from the first stimulation site;
   performing a first stimulation treatment comprising delivering electrical stimulation signals to the first stimulation site through the first electrode lead;
   treating a first pelvic condition of the patient responsive to the first stimulation treatment;
   performing a second stimulation treatment comprising delivering electrical stimulation signals to the second stimulation site through the second electrode lead; and
   treating a second pelvic condition of the patient responsive to the second stimulation treatment.

7. The method of claim 6, wherein:
the control unit comprises a first pulse generator electrically coupled to the first electrode lead, and a second pulse generator electrically coupled to the second electrode lead;
performing a first stimulation treatment comprises generating electrical stimulation pulses using the first pulse generator and delivering the electrical stimulation pulses to the first stimulation site through the first electrode lead;
performing a second stimulation treatment comprises generally generating electrical stimulation pulses using the second pulse generator and delivering the electrical stimulation pulses to the second stimulation site through the second electrode lead.

8. The method of claim 6, wherein:
the control unit comprises a pulse generator and a switch having a first state in which the pulse generator is electrically coupled to the first electrode lead, and a second state in which the pulse generator is electrically coupled to the second electrode lead;
performing a first stimulation treatment comprises placing the switch in the first state, generating electrical stimulation pulses using the pulse generator, and delivering the electrical stimulation pulses to the first stimulation site through the first electrode lead;
performing a second stimulation treatment comprises placing the switch in the second state, generating electrical stimulation pulses using the pulse generator, and delivering the stimulation pulses to the second stimulation site through the second electrode lead.

9. The method of claims 6, wherein implanting electrical stimulation device comprises implanting the one or more electrodes of the first electrode lead in the urinary sphincter of the patient, and implanting the one or more electrodes of the second electrode lead in the anal sphincter of the patient.

10. The method of claim 9, wherein:
treating a first pelvic condition of the patient comprises treating urinary incontinence; and
treating a second pelvic condition of the patient comprises treating fecal incontinence.

11. The method of claim 6, wherein the first and second pelvic conditions are selected from the group consisting of urinary incontinence, fecal incontinence, pain due to interstitial cystitis and urine retention.

* * * * *